US005618727A

United States Patent [19]
Lajoie et al.

[11] Patent Number: 5,618,727
[45] Date of Patent: Apr. 8, 1997

[54] BIOREMEDIATION PROCESS DESIGN UTILIZING IN SITU SOIL WASHING

[75] Inventors: Curtis A. Lajoie, Rockwood; Alice C. Layton, Knoxville; Gary S. Sayler, Blaine, all of Tenn.

[73] Assignee: University of Tennessee Research Corporation, Knoxville, Tenn.

[21] Appl. No.: 399,980

[22] Filed: Mar. 6, 1995

[51] Int. Cl.$^6$ ........................................... B09B 3/00
[52] U.S. Cl. ........................... 435/262.5; 435/262
[58] Field of Search ............................. 435/262.5

[56] References Cited

U.S. PATENT DOCUMENTS

| | | | |
|---|---|---|---|
| 4,843,007 | 6/1989 | Bedard | 435/252.1 |
| 4,978,508 | 12/1990 | Hansen | 422/186 |
| 5,128,262 | 7/1992 | Lindoerfer | 435/264 |
| 5,227,136 | 7/1993 | Hanify | 422/225 |
| 5,342,779 | 8/1994 | Matsumura | 435/262.5 |
| 5,415,777 | 5/1995 | Krempen | 435/262.5 |
| 5,464,771 | 11/1995 | Bryant | 435/262.5 |
| 5,468,628 | 11/1995 | Aust | 435/168 |
| 5,476,788 | 12/1995 | Lamar | 435/262.5 |
| 5,484,729 | 1/1996 | De Weerd | 435/262.5 |

OTHER PUBLICATIONS

Lajoie et al. (1993) *Applied and Environmental Microbiology* 59:1735–41. Development of Field Application Vectors to Express Non–adaptive Foreign genes in Competitive Environments.

J. Fredrickson et al. (1993) *Environmental Science and Technology* 27;1711–1716. In Situ and On Site Bioreclamation.

A. Abdul et al. (1992) *Ground Water* 30:219–231. In Situ Surfactant Washing of Polychlorinated Biphenyls and Oils from a Contaminated Site.

Lajoie et al. (1994) *Applied and Environmental Microbiology* 60:2826–2833. Development of Field Application vectors for Bioremediation of Soils Contaminated with Polychlorinated Biphenyls.

Lajoie et al. (1992) *Applied and Environmental Microbiology* 58:655–663. Development and Use of Field Application Vectors to Express Non–adaptive Foreign Genes in Competitive Environments.

*Primary Examiner*—Carolyn Paden
*Attorney, Agent, or Firm*—Flehr Hohbach Test Albritton & Herbert LLP

[57] ABSTRACT

New strains of microorganisms which posses the dual capabilities for growth on surfactants and degradation of polychlorinated biphenyls are used in combination with soil washing for PCB bioremediation. Soil to be treated is washed with a surfactant to solubilize the generally hydrophobic contaminants. The surfactant solution is then treated in a bioreactor with the microorganisms. As the surfactant is degraded, the residual desolubilized contaminants are adsorbed onto an inert substrate, which is removed from the effluent and can be recycled to the bioreactor.

8 Claims, 5 Drawing Sheets

BIOREMEDIATION PROCESS DESIGN UTILIZING IN SITU SOIL WASHING

This invention was made with Government support under contract TV-90944V awarded by the Tennessee Valley Authority. The Government has certain rights in this invention.

INTRODUCTION

1. Technical Field

The field of this invention is cleansing of contaminated soils through use of bioremediation.

2. Background

Polychlorinated biphenyls are a family of compounds produced commercially by the batch chlorination of biphenyl, which results in mixtures having varying amount of chlorine. Chlorine can be placed at any or all of the ten available sites on the biphenyl nucleus, making 209 theoretically possible PCB congeners. However, due to steric hindrance only about half of these congeners are actually produced. The products vary from light oily fluids with di-, tri-, and tetrachlorobiphenyls, to heavy oils with pentachlorobiphenyls, to greases and waxes of highly chlorinated biphenyls.

The manufacture, importation, distribution and processing of PCBs in the United States was banned in July 1979. Prior to this date, PCBs were heavily used in the electric power industry. PCBs have desirable physical and chemical properties such as low vapor pressure, low water solubility, excellent dielectric properties, stability to oxidation, flame resistance, and are relatively inert. However, the properties which favored their use in electric utilities and other industries have caused their persistence in the environment. Because transformers and capacitors were some of the major uses of PCBs, a number of electric industry sites have PCB contamination in the soil.

Current methods for cleansing soil of PCB contamination have a number of problems. Incineration, on its own, has been generally undesirable process. It is energy inefficient, that is, a large amount of energy is consumed in operating the incinerator at sufficient temperatures and for a sufficient length of time to efficiently purify the volume of material involved. Product gases and materials from the incineration may be a problem. Further, the large amount of contaminated ash formed creates a disposal problem.

Bioremediation shows great promise for ridding the environment of undesirable organic compounds. It makes use of the degradative processes of microorganisms to change organic contaminants into less harmful or undesirable forms. Various strategies have been employed, including promoting growth of microorganisms, inducing metabolic processes which destroy or degrade certain organic compounds, and introduction of exogenous microorganisms into the process. Bioremediation is highly desirable for contaminants such as polychlorinated biphenyls (PCBs) which are currently disposed of by landfilling or incineration.

However, field use of microbial purification have proven unsatisfactory. Few sites have endogenous flora which are capable of PCB degradation. The genes for the biphenyl pathway have been transferred into bacterial strains, allowing for PCB degradation along with biphenyl metabolism. The expression of genes in this pathway is induced by addition of biphenyl to the culture. Attempts to use these highly competent PCB-cometabolizing strains in the environment in the absence of biphenyl have not been successful. However, addition of biphenyl at the waste site is not favored because of its human toxicity and low water solubility.

Field application vectors (FAVs) are a combination of a selective metabolic substrate, a microorganism host, and an expression vector. They have been developed for bioremediation where the microorganism host will be introduced into a competitive environment. Typically, the expression vector will encode exogeneous genes for degradation of an environmental contaminant. Exemplary of such genes are the enzymes for the cometabolism of polychlorinated biphenyls (PCBs) through the biphenyl degradation pathway. The selective metabolic substrate provides a growth advantage to the microorganism. It is of interest to develop means for soil cleansing whereby the use of FAVs many be optimized for bioremediation.

RELEVANT LITERATURE

The development of field application vectors for decontamination of soils containing polychlorinated biphenyls is discussed in Lajoie et al. (1993) *Applied and Environmental Microbiology* 59:1735–41; Lajoie et al. (1992) *Applied and Environmental Microbiology* 58:655–663; Lajoie et al. (1994) *Applied and Environmental Microbiology* 60:2826–2833, and in co-pending U.S. patent application Ser. No. 07/662,735, filed Feb. 28, 1991.

U.S. Pat. No. 4,978,508 provides a method and apparatus for soil decontamination through attrition. U.S. Pat. No. 5,227,136 discloses a bioslurry reactor for treatment of slurries containing minerals, soils and sludges. U.S. Pat. No. 5,128,262 describes microbial decontamination of soils contaminated with hydrocarbons and in particular mineral oils by microbial oxidation.

In situ surfactant washing of polychlorinated biphenyls and oils is described in A. Abdul et al. (1992) *Ground Water* 30:219–231. An overview of in situ bioreclamation may be found in J. Fredrickson et al. (1993) *Environmental Science and Technology* 27:1711–1716.

SUMMARY OF THE INVENTION

Figure 1:
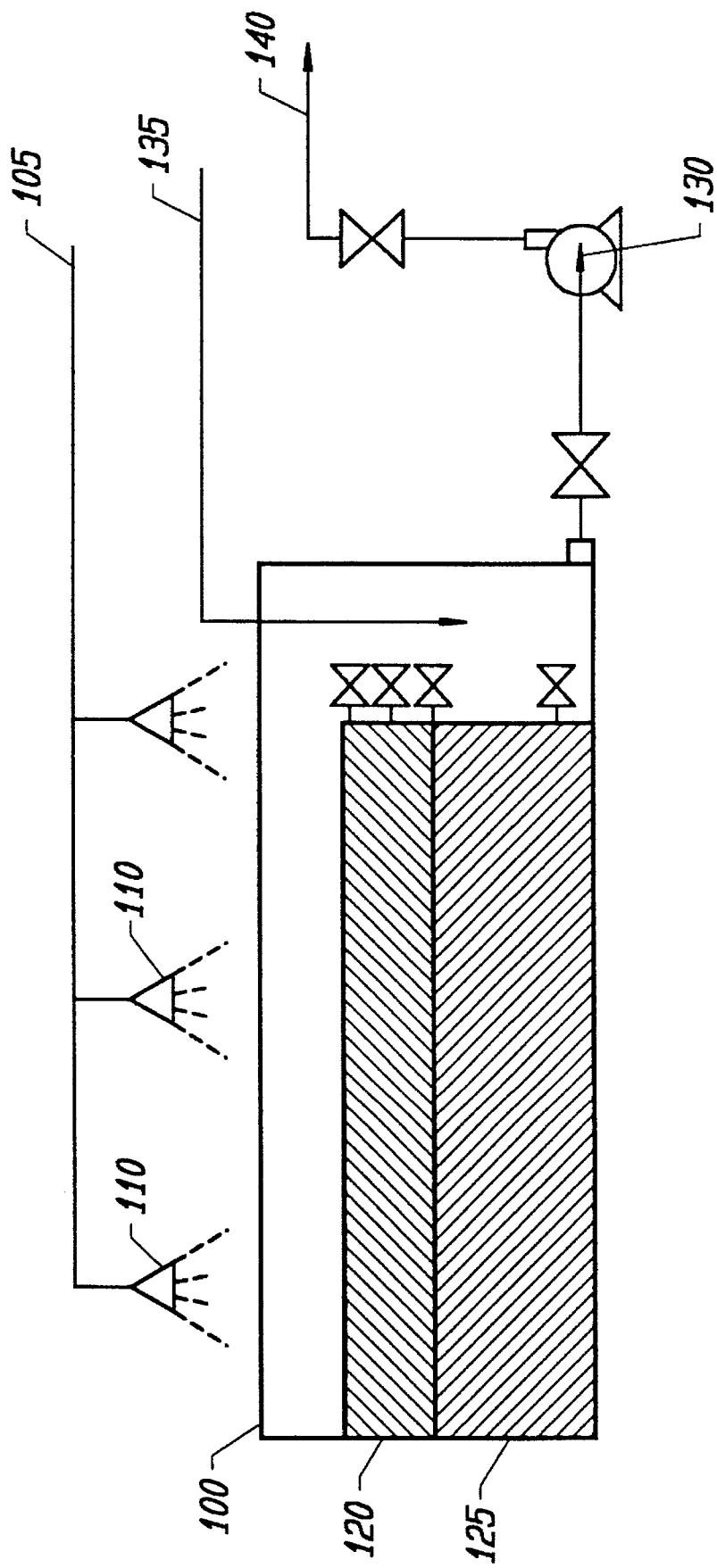
FIG. 1 is a schematic representation of an external reactor cell for the surfactant washing of contaminated soil.

A treatment process for the purification of soils contaminated with PCBs is provided. Soil to be treated is washed with a surfactant to solubilize the generally hydrophobic contaminants. The surfactant solution is then treated in a bioreactor using field application vectors, e.g. recombinant bacterial strains that degrade both the surfactant and the contaminant. As the surfactant is degraded, the residual desolubilized contaminants are adsorbed onto an inert substrate, which is removed from the effluent and can be recycled to the bioreactor.

DESCRIPTION OF THE SPECIFIC EMBODIMENTS

Methods, organisms and DNA compositions are provided for use in the bioremediation of PCB contaminated soils. The contaminated soil is washed in situ with a biodegradable surfactant. The surfactant solution is then treated in a bioreactor to degrade both the surfactant and PCB contamination. Additional reactors are added as necessary to degrade other organic contaminants. As the surfactant is degraded, the residual desolubilized contaminants are adsorbed onto an inert substrate, which is removed from the effluent and can be recycled to the bioreactor.

The subject method is an integrated process where surfactants serve multiple purposes, including enhancing the solubility of hydrophobic chemicals, transporting these chemicals to competent degradative microbial strains, and supporting the selective growth of strains capable of degrading the contaminants. Degradation of the surface micelles results in the enhanced bioavailability and degradation of the micellized contaminants.

The efficacy of the subject method will depend, in part, upon such factors as the nature of the organic contaminants, the nature of the soil itself, the level of toxic contaminants; the presence of other organic or heavy metal contaminants; and the final level of purity desired or required. Determinations of whether, and how, to provide processes according to the present invention will depend, in part, upon analysis of the above factors.

The level of PCB contamination in the soil may be determined by a number of conventional methods. A soil sample will be taken from various positions and depths at the site. Various means of PCB extraction from the contaminated soil sample may be used, including ether extraction, Soxhlet extraction using hexane, rapid, shake flask extraction, or sonication with solvent. The level and composition of PCBs are generally determined by gas chromatography with an electron capture detector.

The subject methods may be used with soils having a wide range of PCB contamination levels. Usually the soil will have about 50 to 500 ppm PCBs. Generally, cleanup is not required for soils having less than about 50 ppm PCBs. Soils may be cleaned that have a very high level of PCBs, because PCBs are relatively inert, and are generally non-toxic to the bacterial strains. Soils having a PCB level greater than about 1000 ppm may require longer washing times or more surfactant solution.

The specific mixture of PCB congeners in the soil will affect the biological degradation. A PCB mixture having a higher concentration of lesser chlorinated biphenyls, such as Aroclor 1242, will be more easily degraded than one with a higher concentration of highly chlorinated biphenyls, such as Aroclor 1254. In such cases, it may be desirable to have an additional reactor for dechlorination of PCBs. Weathering of the PCB may remove the less chlorinated biphenyl compounds, however in the subject cometabolic process the amount of degradation capable for each individual congener over time will be about the same as in an unweathered sample.

Sites may have other organic and/or heavy metal contaminants in addition to the PCB. If biological degradation of other organic contaminants is desired, the subject methods may be modified to include surfactant degrading strains genetically modified with the appropriate contaminant degradative genes. Heavy metal contamination may be treated with microorganism strains capable of sequestering metals, followed by removal of the strains.

The degree of soil contamination will be determined at various depths into the soil, and the depth to which contamination is found will determine the depth of washing necessary. Soil washing to the depth of contamination is required for a complete cleanup. The hydrogeology at contaminated sites is evaluated by drilling wells, and hydraulic conductivity of soils may be determined. The length of time required for water to move through the soil will be shorter for sandy soils than for clay. Soil washing may be conducted both above and below the water table. Methods such as horizontal wells, infiltration trenches, and injection and removal wells may be used to transport solutions through the saturated zone below the water table.

The subject methods are particularly useful for sites containing limestone gravel. PCB can be removed from the interface by surfactant washing without the necessity of excavating the site. Limestone is not very soluble in water so removing the PCB to a reactor via soil washing does not transfer excessive amounts of $CaCO_3$ or other $Ca^{++}$ bases, which require substantial pH adjustment, to the reactor.

While not critical to the practice of the invention, it may be desirable to evaluate the endogenous microbial population. Microbial evaluations may be made to determine total populations, estimate biotransformation potential by means of gene probing to determine the portion of the total population with capacity for degradation of biphenyl and chlorinated biphenyl, identify general microbial population trends, and provide an opportunity to isolate and identify any microbial types which may become prevalent during the field experiment. Evaluations will generally include a determination of total heterotrophs, total fungal spores, PCB-degrading microbial populations, biphenyl, and specific PCB congeners. Such information may be useful in monitoring the effect of the bioremediation process on the site microbial population.

The choice of surfactant is determined by its ability to solubilize PCBs, and by its ability to support the growth of the PCB degrading microorganism. How much PCB is solubilized depends on how much surfactant is absorbed to the soil, and the actual surfactant concentration in solution. Solubilization begins when the critical micellar concentration (CMC) is reached, and increases in surfactant concentration above the CMC. The amount of PCB solubilized by a given amount of surfactant will depend on the soil characteristics and the particular surfactant, and may be determined by small scale testing with soil from the site. The surfactant should be biodegradable to a level such that desolubilization of PCBs occurs in the bioreactor. This level will generally be at about the CMC, and will be affected by surfactant adsorption to cells, soil fines, inert materials or other surfaces in the bioreactor.

Suitable surfactants may be non-ionic or zwitterionic detergents, such as polysorbates, sorbitan esters, polyxamers, polyethylated fatty alcohols, e.g. Brij®, polyethylated fatty acid esters, e.g. Myrj®, and the like. Of particular interest are alkylethoxylates (polyoxyethylene (10) lauryl ether and Brij 30) and alkylphenolethoxylates (Igepal CO-720). Non-ionic alkylated sugar detergents, e.g. n-decyl β-D-glucopyranoside, n-dodecyl β-D-glucopyranoside, n-dodecyl β-D-maltoside, n-heptyl β-D-glucopyranoside, n-octyl β-D-glucopyranoside, n-octyl α-D-glucopyranoside, n-nonyl β-D-glucopyranoside, etc. or anionic detergents may also be used.

The contaminated soil is washed with a solution of biodegradable surfactant and water. The surfactant will be applied at a concentration greater than the CMC, in order to maximize the washing. The concentration will usually be at least about 0.1% weight/volume surfactant, and may be as high as about 5%, depending on the particular CMC. The solution is applied on to the soil until the soil is saturated. The surfactant solution is drawn through the soil, by pumping, etc., and collected in a reservoir. This cycle is generally repeated several times over the course about 2 to 3 days, and may be repeated for a week or more. The washing removes at least about 25% of the PCBs from the soil, more usually at least about 50%, and preferably at least about 70%. Additional rounds of washing may be required for heavily contaminated soils, using fresh surfactant solution. It may be desirable before or during the washing process to mix and/or loosen the soil by rototilling, etc. to further ensure penetration of surfactant. In some cases it may be desirable to excavate the soil, and perform the washing in an enclosed area, as described with reference to FIG. 1.

FIG. 1 is a schematic of a soil washing cell. The cell is advantageous in that less monitoring is required to determine if the washing solution is migrating deeper into the subsurface or laterally off-site. The cell 100 consists of an irrigation pump configuration for supplying surfactant to the soil 110 through which a surfactant solution stream 105 is applied to the contaminated dirt 120 over a layer of clay 125. A collection pump 130 transports collected effluent into a bioreactor system stream 140. Nutrients sources 135 of nitrogen and phosphorus for microbial growth may be added to the effluent. Surfactant and water are circulated through the soil in the cell via the soil irrigation system until PCB concentration in solution reaches a steady maximum concentration, usually at least about 2 days and usually not more than about 7 days.

The surfactant solution containing solubilized PCB and other contaminants is pumped to a bioreactor for treatment with the field application vector (FAV) microbial strain. A single bioreactor may use one or a cocktail of FAV strains. The FAV strain will be capable of degrading a wide range of PCBs to their corresponding chlorobenzoic acids. The effective range of degradation may be enhanced by an initial dechlorination of PCB congeners through anaerobic treatment, to a level of chlorination degradable by the FAVs. During the PCB biotransformation, the strain will also biodegrade the surfactant. As the surfactant is degraded, the solubilized PBCs are desolubilized, and will deposit upon an inert substrate in the bioreactor.

The inert substrate is inert with respect to microbial degradation, i.e. it should not be degraded to the point that it will result in significant oxygen depletion or be degraded before it can be filtered or settled out with its load of residual recalcitrant PCBs. Suitable substrates include diatomaceous earth, fine sand, ceramic or plastic particles, sawdust, woodchips or other slowly degradable or inert materials that can be separated from the aqueous phase by settling, flotation or filtration. The cells that result from growth on surfactant will also act as an inert substrate, i.e. after desolubilization by surfactant degradation the residual PCBs may stick to the cells, which can be filtered out of the aqueous stream.

Suitable microbial strains for the FAV will be capable of utilizing surfactant as an energy source. The ability to grow on surfactant may be determined empirically by inoculating a culture medium with the desired surfactant at a concentration from 0.02 to 0.2% and quantitating the biodegradation. Preferably, the surfactant will be completely degraded by the particular strain. For regulatory purposes, strains should be nonpathogenic. The microbe will usually be a bacteria, more usually a gram-negative bacteria. Genera of interest include Alcaligenes sp., Pseudomonas sp., Burholderia sp. The strain will either have endogenous genes capable of PCB degradation, or be competent for transformation, i.e. by conjugative mating, transposon transfer, transfection, viral infection, etc. Of particular interest are the surfactant degrading strains *Alcaligenes eutrophus* strain B30P4; *Pseudomonas putida* strain IPL5.

Exemplary enzymes for PCB degradation are encoded by the biphenyl dioxygenase operon, bphABCD. The operon is highly conserved among soil bacteria (see Yates and Mondello [1989] *J. Bacteriol Mar* 171;1733–5). Of particular interest is the bphABCD operon form LB400 and closely related operons, which have a broad specificity, i.e. degrades a high number of individual PCB congeners. Strains having an endogenous biphenyl pathway include *Burkholderia gladioli* strain NE-2; *Alcaligenes eutrophus* strains ENV307 and GG4202, Pseudomonas sp. LB400; *Pseudomonas cepacia* ET4, etc. The presence of the biphenyl pathway in an unidentified strain may be determined by hybridization with DNA from one of the known bph operons under conditions that allow detection of DNA having at least about 70% homology over one of the bph genes, or by determining the ability of the microorganism to grow on biphenyl. Colonies may also be selected on the basis of their ability to convert 2,3-dihydroxybiphenyl to the yellow meta-cleavage product.

Figure 2:
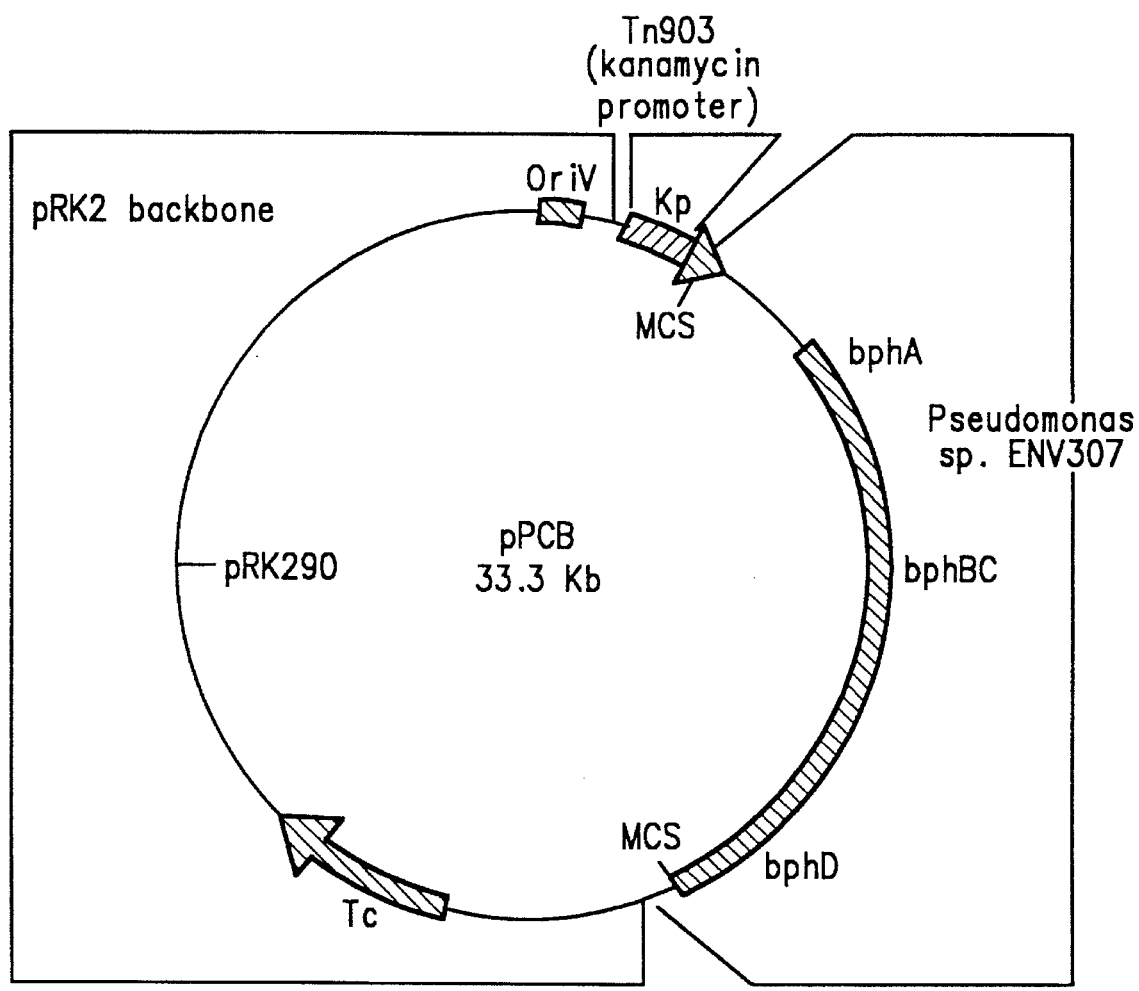
FIG. 2 is a map of the plasmid pPCB.

Conveniently, and DNA vector will be constructed containing the genes encoding the PCB degrading enzymes. It is preferable to use an exogenous source for the PCB degradation pathway because the expression may be artificially regulated, and it allows greater freedom in the selection of a suitable host. The expression of the genes may be placed under the control of a constitutive promoter, or one induced by a simple organic compound, e.g. lactose, IPTG, etc. In this way, expression is decoupled from biphenyl induction. In one preferred embodiment, the expression of the PCB degradation pathway will be under the regulatory control of the surfactant degradation promoter. The vector may be episomal or integrative, e.g. a plasmid, usually having a broad host range origin of replication; a transposon; and the like. An example of a suitable plasmid is described in the experimental section and illustrated in FIG. 2. Plasmid pPCB contains the bphABCD operon from *Alcaligenes eutrophus* strain ENV307 on a broad host range vector.

Figure 3:
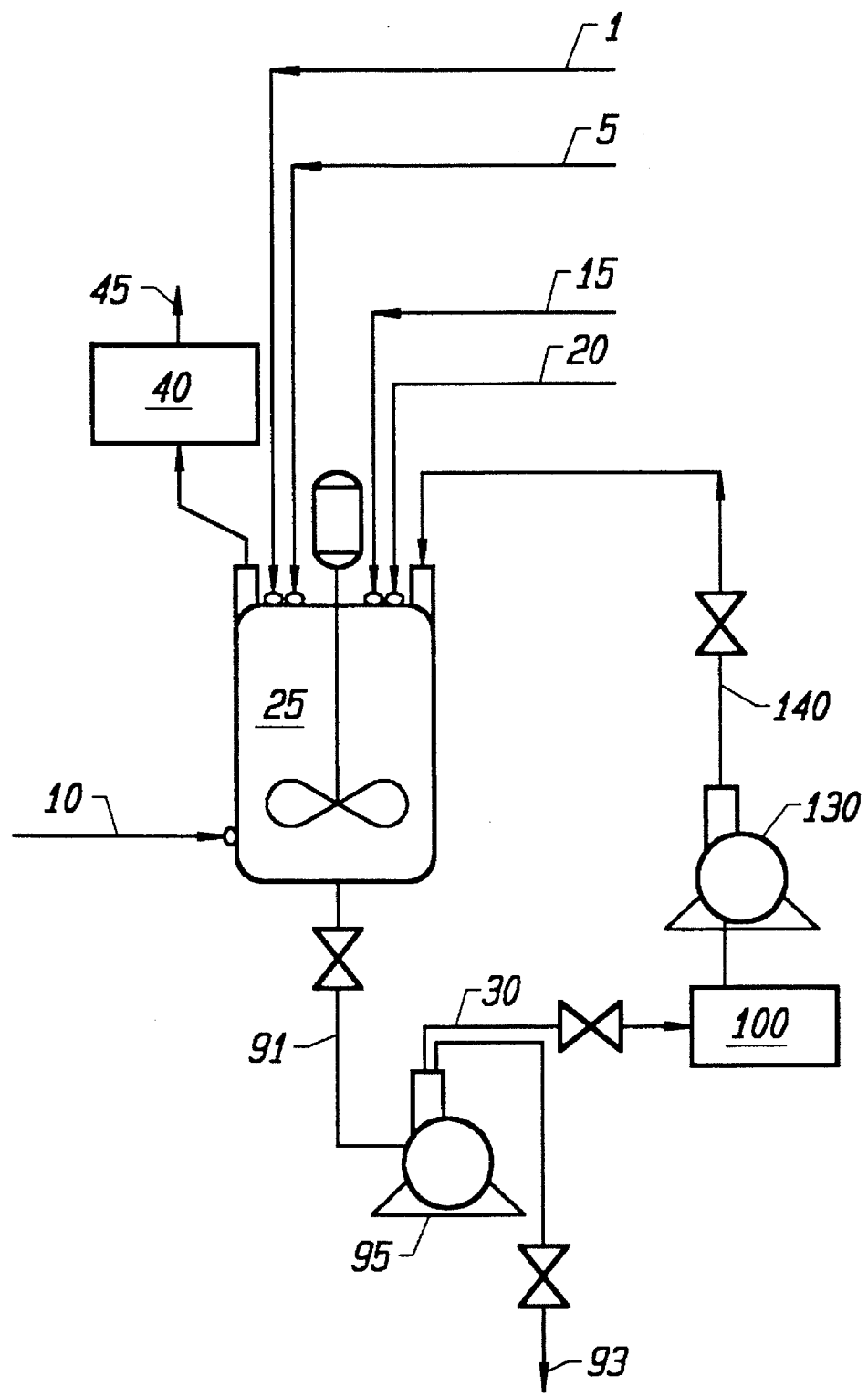
FIG. 3 is a schematic representation of a bioreactor for growing the field application vector strains.

FIG. 3 is a schematic of a bioreactor for the field application vector biotransformation. The bioreactor 25 is inoculated with the FAV strain(s). Water 1, nutrients, e.g. nitrogen, phosphorus, micronutrient fertilizer, 5; air 10; and return surfactant solution from soil washing 15 are input to the bioreactor. An inert substrate 20 is also input. A collection pump configuration 130 transports collected effluent from the soil washing cell 100 (containing surfactant and solubilized PCBs), as described in FIG. 1, and feeds into the bioreactor system stream 140 to bioreactor input 15. The bioreactor has outputs to the atmosphere 45 through an activated charcoal filter 40. A collection pump configuration 95 transports the bioreactor effluent 91 into the waste stream 93, or recycling into the soil washing stream 30. Surfactant may be added to the bioreactor effluent 30 to begin another round of soil washing.

The pH of the solution in the bioreactor is determined and adjusted to a range of about 6.5–7.5, if necessary. The reactor is inoculated with genetically engineered FAV strains. The solution in the reactor is aerated and mixed until the surfactant is completely degraded. The degree of PCB degradation will depend on the specific mix of congeners, but is generally considerably slower than surfactant degradation. When the surfactant is degraded, usually at least about 50% of PCBs present will be degraded to their corresponding chlorobenzoic acids, more usually at least about 75% will be degraded. The length of time necessary will be determined by the cell number and activity of the FAV strain, the amount of PCBs present, the presence of other contaminants in the effluent, the temperature, and the amount of surfactant and other nutrients present. Usually the incubation will take at least about 5 days, more usually at least about 10 days, and may be as long as about 20 days.

The progress of the bioreaction may be monitored by quantitating the amount of PCBs present both in solution and deposited on the inert substrate. PCBs are determined by ether extraction and congener specific gas chromatography. Surfactant concentration may also be monitored, by determination of cobaltothiocyanate active substances (CTAS, Standard Methods for Examination of Water and Wastewater). Those congeners that are not degradable by the FAV strain are concentrated by deposition on an inert substrate and removed from the wash solution for further treatment, e.g. anaerobic dechlorination, aerobic degradation by other PCB degrading strains, UV photodegradation, etc., before recycling back to the bioreactor for further degradation.

In order to fully degrade the PCBs present, an additional aerobic microorganisms may be introduced in a second bioreactor. The culture will have an active PCB degradation pathway, usually through co-metabolism with biphenyl. Species of interest include *Phanerochaete chrysosporium*, *Pseudomonas sp.*, *Alcaligenes eutrophus*, and Corynebacterium. The presence of the biphenyl pathway in a microorganism may be determined as described above. Incubation is continued until all degradable PCB congeners are eliminated, biphenyl disappears, and further addition of biphenyl does not result in additional PCB degradation.

In order to fully degrade the PCBs, it will usually be necessary to perform a dehalogenation step. The inert substrate containing PCBs is moved to a bioreactor with an inoculum of an anaerobic consortium, and incubation is conducted without stirring and aeration. Anaerobic organisms that exhibit dehalogenating activity are known in the art, but have not been classified or isolated. Generally, sediments from a natural site exhibiting dehalogenating activity, e.g. Hudson River sediments are used for inoculation. Anaerobic dechlorination is slower process than aerobic degradation, where the retention time for anaerobic dechlorination is at least about 1 month, usually at least about 2 months. Effective dechlorination is indicated by a shift in GC congener profiles, i.e. a decrease in high molecular weight PCBs and a corresponding increase in lower molecular weight PCBs. Incubation may be continued until no further shifts in congener patterns are observed.

Figure 4:
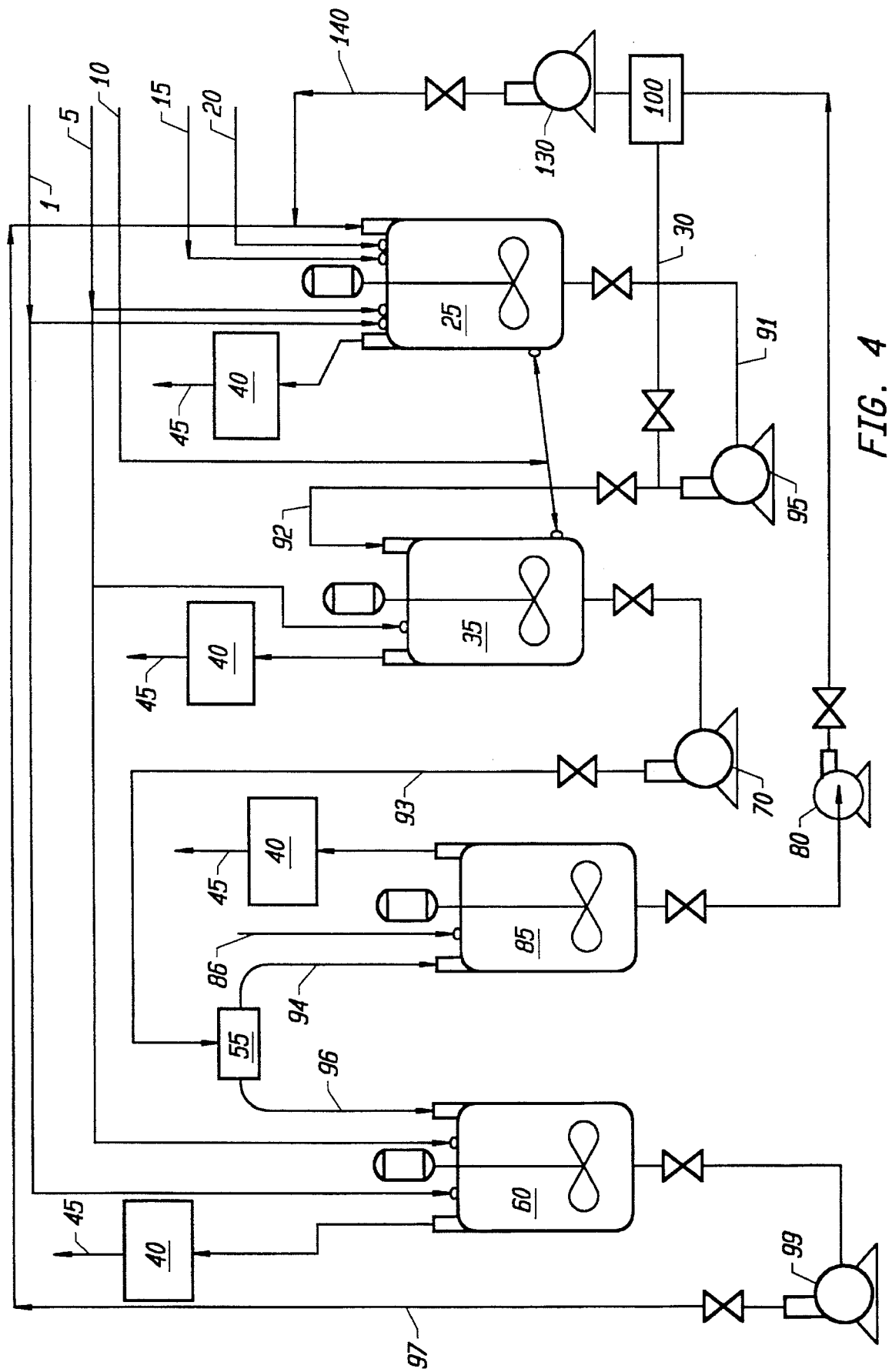
FIG. 4 is a schematic representation of a complex bioreactor process.

FIG. 4 is a schematic flow diagram for a multiple bioreactor process. Three bioreactors are used. The bioreactor 25 for the FAV strain(s) will transform PCBs to chlorobenzoic acid in the presence of surfactant and the absence of biphenyl. An optional second bioreactor 35 uses aerobic biphenyl cometabolising strain(s) to cometabolize PCBs in the presence of biphenyl. A holding tank 85 may be provided. The third bioreactor 60 provides for anaerobic dechlorination of residual PCBs not degraded by the aerobic strains, which are then recycled to bioreactor 25 for aerobic degradation to chlorobenzoic acids.

Chlorobenzoic acids result from the aerobic degradation of PCBs. They may be degraded by naturally occurring organisms entering the bioreactor in the soil wash solution. Optionally, organisms that degrade them are added to reactor 35, such that additional PCB degradation by naturally occurring strains with biphenyl, and chlorobenzoate degradation occur concurrently. Chlorobenzoic acid degrading strains include some Pseudomonas and Arthrobacter species. Chlorobenzoic acid degrading strains are also likely to be found in sediments added for anaerobic degradation.

The inputs to the FAV strain bioreactor 25 are as described in FIG. 3. Nutrients 5 and air 10 are provided as inputs for the biphenyl cometabolism bioreactor 35. Water and nutrients are provided as inputs for the anaerobic bioreactor 60. As described in FIG. 3, outputs to the atmosphere 45 through an activated charcoal filter 40 are provided for each bioreactor.

A collection pump configuration 130 transports collected effluent from the soil washing cell 100, as described in FIG. 1, and feeds into the bioreactor system stream 140. The effluent is processed in the FAV strain bioreactor 25. The bioreactor effluent 91 is transported through a pump configuration 95 to the biphenyl cometabolism bioreactor input stream 92 or is recycled into the soil washing stream 30. From the bioreactor 35 the effluent 93 is transported through a pump 70. The inert substrate and cells from the previous bioreactors are removed from the process stream 93 by a filter 55. The filtered effluent 94 then enters holding tank 85, is further amended with surfactant, and is returned to the soil washing cell via pump 80 for further soil washing. The inert substrate is directed 96 to an anaerobic bioreactor 60 for dechlorination. The final effluent may be transported through a pump configuration 99 to the waste stream 97, or recycled through the process.

Input of an inert substrate 20 is provided for the bioreactor 25. As the surfactant is degraded, the remaining PCBs will deposit on the substrate. The substrate, e.g. inert substrate plus adsorbed and concentrated PCBs, is then removed from the aqueous reactor stream 55 for anaerobic dechlorination 60, recycling to the aerobic reactors 25 or 35 for further degradation before or after anaerobic treatment, and/or for disposal and incineration.

The overall progress of the soil cleansing will be monitored by soil analysis and analysis of the effluent streams from the various bioreactors. It is necessary to reduce PCB concentration to a level acceptable to the appropriate regulatory authorities, e.g. EPA. This can be a specific concentration or a level based on risk analysis. The proof of accomplishment of this objective is the reduction of PCB concentration after treatment. It is recognized that PCBs are a mix of compounds consisting of the biphenyl molecule chlorinated at varied positions and having varied degrees of chlorination. The evidence of biotransformation is change in the total congener mass balance as a result of the application of the process.

PCBs may be analyzed as described previously and reported on a weight per interface or bioreactor medium basis. A mass balance may be calculated from data generated from analysis of initial and final samples. In addition, time course samples may be used to monitor and to predict application of the phased reactions described in the in situ soil irrigation process: (1) PCB release by the action of the surfactant, (2) PCB biotransformation resulting from the recombinant microorganism in the presence of the surfactant, (3) PCB biotransformation resulting from the addition of biphenyl and known PCB-degrading strains, and (4) anaerobic dechlorination.

The following examples are offered by way of illustration and not by way of limitation.

EXPERIMENTAL

EXAMPLE 1

Construction of FAV Strains

Identification of bacterial strains

Microorganisms were identified taxonomically by two independent testing laboratories and at the University of Tennessee. Microcheck, Inc. (Northfield Vt.) identifies bacteria by fatty acid analysis, and Analytical Services, Inc. (Essex Junction, Vt.) identifies bacteria using the Biolog Database system. At UT the bacteria were identified using diagnostic tests and carbon utilization from Bergey's manual of Systematic Bacteriology Vol. 1.

The strains tested were ENV307; GG4202; B30P4; NE2-1and IPL5. *Alcaligenes eutrophus,* B30P4:: TnPCB, Accession Number 55827, was deposited in the American Type Tissue Collection, 12301 Parklawn Drive, Rockville Md. 20852, under the conditions of the Budapest treaty on Oct. 1, 1996. *Pseudomonas putida*, IPL5:TnPCB, Accession Number 55828, was deposited in the American Type Tissue Collection, 12301 Parklawn Drive, Rockville Md. 20852, under the conditions of the Budapest treaty on Oct. 1, 1996. The strains ENV307, GG4202, and B30P4 probably belong to the genus Alcaligenes. The results indicate that GG4202 and ENV 307 are both *Alcaligenes eutrophus*. B30P4 is an Alcaligenes species, although the species identification differed. Analytical Services identified B30P4 as an unidentified group called CDC Group IVC-2.

TABLE 1

Summary of Taxonomic Identifications

| Strain/Use | Microcheck | Analytical Services | University of Tennessee |
|---|---|---|---|
| ENV307<br>Source of<br>bphABCD genes | Alcaligenes eutrophus | Comamonas acidovorans*** | Alcaligenes eutrophus |
| IPL5<br>Surfactant Strain | Pseudomonas chlororaphis<br>**(Pseudomonas sp.) | Pseudomonas putida Type A1* | Pseudomonas putida |
| B30P4<br>Surfactant Strain | Alcaligenes eutrophus* | CDC Group IVC-2* | Alcaligenes denitrificans<br>subspecies denitrificans |
| NE2-1<br>Biphenyl Strain | Pseudomonas cepacia***<br>(renamed Burkholderia<br>cepacia) | Not tested | Burkholderia gladioli<br>(basonym: Pseudomonas<br>gladioli) |
| GG 4202<br>Biphenyl Strain | Alcaligenes eutrophus** | Not tested | Alcaligenes eutrophus |

\* = Excellent Match
\*\* = Good Match
\*\*\* = Poor Match

Strain NE2-1 was identified as *Pseudomonas cepacia* (reclassified as *Burkholderia cepacia*) by Microcheck. This identification is similar to the identification of the strain as *Burkholderia gladioli* by UT. Burkholderia is the new genus classification for several Pseudomonas species including (*P. cepacia, P. picketti, P. gladioli, P. solanacearum*) (*International Journal of Systematic Bacteriology.* 43:398–399, 1993).

Construction of the PCB vectors

The PCB degradative genes were cloned from strain ENV307. Large fragments from Sau3A partial digests of chromosomal DNA from ENV307 were ligated into the BamHI site of cosmid cloning vector pHC79 (Bethesda Research Labs). The cosmids were then packaged with an in vitro packaging system (Gigapak, Stratagene). The resulting λ phage were used to transduce *E. coli* MC1061, and transductants were selected on plates supplemented with ampicillin. Clones containing PCB-degradative genes were selected on the basis of their ability to convert 2,3-dihydroxybiphenyl to the yellow meta-cleavage product. The restriction fragments containing the biphenyl-degradative genes were subcloned into *E. coli* vector pUC19.

An XhoI-HindII fragment from the multiple cloning site of pGEM-7zf(−) was cloned into the XhoI-HindII region of the broad host range plasmid pRK293, eliminating 0.5 kb from the kanamycin resistance gene. The resulting plasmid (pPCL1) contains two EcoRI sites. Plasmids pPCL1 and pUC19PCB were partially digested with EcoRI, ligated, and transformed into *E. coli*. The kanamycin promoter and bph genes were cloned from the resulting plasmid (pCL3) into pUC18Not via a HindII-partial BglII digest. The bphD gene was added via partial ClaI digests. Plasmid pPCB (shown in FIG. 2) was produced by cloning the bphD gene from pUC18NotPCB into pCL3 via partial ClaI digests (see Lajoie et al. [1994] infra.).

The transposon TnPCB was formed by replacing the luxAB genes of the transposon mini-Tn5 with the kanamycin promoter-bphABCD fragment via NotI digests.

Restriction mapping analysis indicates that the PCB degradation genes of ENV307 are extremely similar if not identical to the PCB genes from Pseudomonas LB400 (bph locus). The entire bph locus from LB400 has been sequenced (Erickson and Mondello [1992] *J. Bacteriol.* 174:2903–2912 and Hofer et al. [1993] *Gene* 130:47–55, 1993). The size of the bph locus from LB400 is 12.5 kb. Restriction maps of the ENV307 PCB genes are in good agreement with this size. The bphA gene begins 1.4 kb downstream from the first EcoRI site. The bphD gene ends at the last EcoRI site.

Plasmid Preparation and Bacterial Transformation

Plasmid preparations: Large and small scale plasmid preparations were performed on strains IPL5, IPL5::TnPCB, IPL5 (pPCB), B30P4, B30P4::TnPCB and B30P4 (pPCB). The plasmid pPCB could be isolated from both strains IPL5 (pPCB) and B30P4 (pPCB) in small scale preparations. Efforts to isolate plasmids from IPL5::TnPCB or B30P4::TnPCB using large scale plasmid preparations did not indicate the presence of endogenous plasmids.

Transfer of plasmids into surfactant degrading strains. Transfer of plasmids was performed as described in Lajoie et al. (1993), infra. Briefly, the recipient strains IPL5 and B30P4 were grown in a triparental mating with *coli* HB101 containing the helper plasmid (pRK2013) and *E. coli* DH5α isolates carrying pPCB. Successful mating was indicated by colonies which turned yellow when they were sprayed with 2,3-dihydroxybiphenyl.

Matings were performed to determine if the PCB degradative genes in the recombinant surfactant degrading strains were transmissible. The plasmid pPCB is not a self transmissible plasmid and requires a helper plasmid (such as pRK2013) in order to be transferred by conjugation. The donor strains for these experiments were IPL5::TnPCB, IPL5 (pPCB), B30P4::TnPCB, and B30P4 (pPCB). The recipient was a rifampicin resistant *Pseudomonas putida* strain PB2240. Triparental matings between *E. coli* DH5α(pPCB), *E. coli* DH5α(pRK2013) and *P. putida* PB2240 were performed as a positive control to insure that this strain could function as a recipient for the PCB degradative genes. Individual strains were plated on the selective media for mating mixtures to insure that spontaneous antibiotic resistant mutants did not yield false positives. Matings were also performed to determine if the ability to utilize surfactants as growth substrates were transmissible. Negative controls were again utilized, but it was not possible to employ positive controls, since surfactant degrading genes have not been isolated from either of the surfactant degrading strains.

The strains were grown on the following media: *P. putida* IPL5 (TnPCB) and IPL5 (pPCB) on 0.2% Igepal C0-720/ PAS/ tetracycline (10 ppm); *A. denitrificans* B30P4 (TnPC18) and B30P4 (pPCB) on 0.2% Polyoxyethylene 10 lauryl ether /PAS/ tetracycline (10 ppm); *P. putida* PB2440 on LB/rifampicin (100 ppm), *E. coli* DH5 (pPCB) on LB/tetracycline (10 ppm) and *E. coli* DH5(pRK2013) on LB kanamycin (60 ppm). Matings were performed for 24 hours at 27° C. on YEPG plates. Mixtures were scraped from plates, resuspended in buffer, and plated on duplicate selective media agar plates. Selective media plates were incubated at 27° C., and colonies were counted at 3 and 7 days.

TABLE 2

Number of bacterial colonies obtained from mating experiments.

| Mating Mixtures | YEPG tetracycline (25 PPM), rifampicin 100 ppm) 3 days/7 days | 0.2% Polyoxyethlene 10 laury ether/ PAS/rifampicin (100 ppm) 3 days/7 days | 0.2% Ipegal CO-720/PAS/rifampicin (100 ppm) 3 days/7 days |
|---|---|---|---|
| Negative Controls | | | |
| pB2240 | 0,0/0,0 | 0,0/0,0 | 0,0/0,0 |
| DH5a(pPCB0), DH5a(pRK2013) | 0,0/0,0 | NA | NA |
| IPL5 (pPCB) | 0,0/0,0 | NA | 0,0/2,1 |
| B30P4 (PPCB) | 0,2/0,3 | 0,0/1,4 | NA |
| Positive Control | | | |
| DH5a(pPCB) DH5a(pRK2013) pB2240 | >100, >100/>100, >100 | NA | NA |
| Experimental | | | |
| IPL5(pPCB),pB2240 | 0,0/0,0 | NA | NA |
| IPL5(TnPCB), pB2240 | 0,0/0,1 | NA | 0,0/2,1 |
| B30P4(pPCB), pB2240 | 0,0/0,0 | NA | NA |
| B30P4(TnPCB), pB2240 | 0,0/0,0 | 0,0/4,4 | NA |
| B30P4,pB2240 | 0,0/0,0 | 0,0/2,1 | NA |

Neither the plasmid pPCB nor the transposon TnPCB, containing the tetracycline resistance gene, were transferred from either IPL5 or B30P4 to the recipient stain pB2240. Therefore, if there are other plasmids in strains IPL5 and B30P4 they did not mobilize plasmid pPCB. The transfer of the PCB degradative genes separate from the tetracycline resistance gene seems unlikely. Transfer of surfactant degradative genes is not indicated at day 3. By day 7, a few colonies grew on both the negative control plates [B30P4 (pPCB) and IPL5 (pPCB)] and the experimental plates containing surfactant and rifampicin. The phenotypes of these colonies were checked and were determined to be spontaneous rifampicin mutants of the original surfactant degrading strains.

Growth of FAV strains on Surfactant. The FAV strain were grown on nonionic surfactants (alkylethoxylate and alkylphenolethoxylate type) and other substrates similar in structure to the moieties present in these nonionic surfactants to determine if they could support their growth, and if any degradation products accumulated in the growth medium. All substrates were added to PAS medium at a concentration of 0.2%, and incubations were performed at room temperature. After a 10-day incubation, cultures showing visible growth were extracted using a hexane-ether mixture, and the extracts analyzed by gas chromatography using a flame ionization detector. Extracts exhibiting peaks were further analyzed by comparison with known standard chemicals and by gas chromatography/mass spectroscopy. The test substrates, presence or absence of visible growth, and any observed degradation products are indicated below.

TABLE 3

Growth of surfactant degrading strains on different growth substrates and resulting degradation products

| | Pseudomonas putida 1PL5 | | Alcaligenes eutrophus B30P4 | |
|---|---|---|---|---|
| Substrates*[1] | Growth | Products | Growth | Products |
| Igepal CO-720 (nonylphenolethoxylate) | + | nonylphenoldiethoxylate | − | NA |
| Polyoxyethylene 10 lauryl ether (alkylethoxylate) | + | 2-(dodecyloxy)-ethanol | + | none |
| Brij 30 (alkylethoxylate) | + | 2-(dodecyloxy)-ethanol | + | none |
| Igepal Co-210 (nonylphenoldiethoxylate) | − | NA | − | NA |
| Dodecane | − | NA | − | NA |
| 1-Dodecanol | + | none | + | none |
| Nonane | + | NA | − | NA |
| a-Nonanol | + | none | − | NA |
| Polyethylene glycol (Avg. mol. wt. 200) | + | none | + | none |

Results of substrate degradation experiments indicate that *Pseudomonas putida* IPL5 utilizes both alkylethoxylate and alkylphenolethoxylate surfactants as growth substrates. Although this strain can utilize 1-dodecanol and 1-nonanol for growth, it cannot use these moieties when present in the surfactants, and the polyoxyethylene side chain is not completely degraded. This results in accumulation of alkylphenoldiethoxylates or 2-(dodecyloxy)-ethanol from the alkylphenolethoxylate or alkylethoxylate surfactants, respectively.

*Alcaligenes eutrophus* B30P4 utilizes alkylethoxylate surfactants as growth substrates, but cannot degrade the alkylphenolethoxylate surfactant. In contrast to *Pseudomonas*

*putida* IPL5, *Alcaligenes eutrophus* B30P4 appears to completely degrade the alkylethoxylate surfactants, and grows readily on polyethylene glycol.

PCB degradation by the recombinant strains determined in resting cell assays.

Resting cell assays were performed on strains B30P4::TnPCB and IPL5::TnPCB (Table 4, columns 3 and 4) by growing the strains in surfactant and transferring them to non-growth conditions with 10 ppm Aroclor 1242. After a 2 day incubation with shaking the residual PCB were extracted to determine the amount of PCB degraded. This assay is used as measure of enzyme activity independent of cell growth. Both strains have the capability of degrading a large number of congeners as indicated in Table 4.

PCB degradation in surfactant solution.

Experiments were conducted to determine the extent of PCB degradation in surfactant [polyoxyethylene (10) lauryl ether] solution by the FAVs *Pseudomonas putida* IPL5::TnPCB and *Alcaligenes eutrophus* B30P4TnPCB (Table 4, column 5). In these experiments 5 ml PAS medium was amended with 0.025 g diatomaceous earth, 25 ppm Aroclor 1242 (PCBs), and 2,000 ppm surfactant. Experimental tubes were inoculated with approximately $10^6$ cells/ml of each of the recombinant strains. Controls remained uninoculated. Both experimental and control tubes were prepared in triplicate. Incubation was at room temperature on a rotary incubator for 20 days after which surfactant and PCB concentrations were determined. Surfactant analysis was performed using the cobaltothiocyanate active substances method (CTAS; Standard Methods for Examination of Water and Wastewater). PCBs were extracted using ether, and the extract was further purified using silica gel. PCBs were quantified using congener specific capillary gas chromatography with an electron capture detector. PCB concentrations were determined by comparison to peak areas using known concentrations of an Aroclor 1242 standard. Standard deviations (SD) of surfactant and PCB concentrations were determined from individual determinations from triplicate experimental or control tubes.

After incubation the final surfactant and PCB concentrations in the control were 2122 ppm (SD 4) and 27.7 ppm (SD 0.21), respectively. Final surfactant and PCB concentrations in the inoculated experimental tubes were 225 ppm (SD 2) and 6.4 ppm (SD 0.61), respectively. Congener specific PCB concentrations are indicated in Table 4. These results indicate that the recombinant strains (FAVs) degraded the surfactant and PCBs in a solution containing surfactant, PCBs, and diatomaceous earth.

Removal of PCBs from soil by surfactant washing.

PCB contaminated soil from an electric power substation was washed with an equal volume of 10,000 ppm polyoxyethylene (10) lauryl ether (ml surfactant solution/g soil). The surfactant solution was sprayed on the soil until the soil was saturated causing ponding. The surfactant solution was drawn through the soil by use of a pump and collected in a reservoir. This cycle was performed for two days. 65 ppm of PCB out of an initial concentration of 90 ppm of PCB in the soil was obtained in the soil wash solution (71% recovery).

Degradation of PCBs in soil surfactant wash solution.

The surfactant wash solution derived from the above soil washing experiment was subsequently used for biodegradation experiments. Because of the nature of the PCB contamination in soils from this particular sites the PCB congener pattern contains a much higher percentage of high molecular weight PCB congeners than that found in Aroclor 1242. The soil wash solution was adjusted to pH 7 and amended with the same nutrients as present in PAS medium (nitrogen, phosphorus and trace elements). The solution (1 ml) was then added to 4 ml PAS medium in 15 ml culture tubes (5 ml per tube) and amended with 0.025 g diatomaceous earth. Triplicate tubes were immediately analyzed for PCB concentration [Time 0($T_0$) tubes] by the method described above. Triplicate tubes also remained uninoculated (control tubes) or were inoculated with *Pseudomonas putida* IPL5::TnPCB and *Alcaligenes eutrophus* B30P4::TnPCB (experimental tubes) as described above. Control and experimental tubes were incubated for 14 days at room temperature on a rotary incubator. After incubation PCB concentrations were determined as described above.

Initially ($T_0$) the PCB concentration was 9.3 ppm (SD 0.7). After 14 days the corresponding concentrations in the inoculated experimental tube was 6.2 ppm (SD 0.5). The PCB concentration in the uninoculated control was 8.8 ppm (SD 1.1). The percentages degraded for the specific congeners are indicated in Table 4 column 6. These results indicate that 34% PCB degradation occurred in the inoculated experimental tube, whereas no statistically significant PCB degradation was observed in the uninoculated control. The FAVs were able to cometabolize PCBs removed from the soil by surfactant washing. Degradation is considerable, although not as dramatic as that observed in experiments using Aroclor 1242 due to the much higher proportion of high molecular weight PCBs in this particular contaminated soil.

TABLE 4

Performance of the strains B30P4::TnPCB and IPL5::TnPCB in resting cell assays, growing cell assays with 1242 (25 ppm), and a surfactant-PCB washate from PCB contaminated soil.

| | | Resting Cell Assays[a] | | | |
| Peak # | Congener | B30P4::TnPCB | IPL5::TnPCB | Growing Cell Assay[b] | Surfactant/PCB Washate[c] |
| --- | --- | --- | --- | --- | --- |
| 2 | 2,2'/2,6 | 87 | >97 | >90 | —* |
| 3 | 2,4/2,5 | >98 | >98 | >95 | — |
| 4 | 2,3' | >98 | >98 | >95 | — |
| 5 | 2,3/2,4' | >99 | >99 | >99 | — |
| 6 | 2,6,2' | 0 | 20 | 90 | — |
| 7 | 2,5,2' | 90 | 95 | >99 | — |
| 8 | 2,4,2'/4,4' | >99 | >99 | >99 | — |
| 9 | 2,3,6/2,6,3' | 50 | 80 | >95 | — |

TABLE 4-continued

Performance of the strains B30P4::TnPCB and IPL5::TnPCB in resting cell assays,
growing cell assays with 1242 (25 ppm), and a surfactant-PCB washate from PCB
contaminated soil.

| Peak # | Congener | Resting Cell Assays[a] | | Growing Cell Assay[b] | Surfactant/ PCB Washate[c] |
|---|---|---|---|---|---|
| | | B30P4::TnPCB | IPL5::TnPCB | | |
| 10 | 2,3,6/2,6,3' | 60 | 60 | >99 | >35 |
| 11 | 2,5,3' | 95 | >99 | >98 | — |
| 12 | 2,4,3' | 70 | >99 | >98 | — |
| 13 | 2,5,4 | >99 | >99 | 90 | — |
| 14 | 2,4,4' | 25 | 30 | 85 | 65 |
| 15 | 2',3,4/2,5,2',6' | 90 | 95 | 98 | >65 |
| 16 | 2,3,4'/2,4,2',6' | 30 | 75 | 95 | >90 |
| 17 | 2,3,6,2' | 35 | 50 | >99 | >80 |
| 18 | 2,3,2',6' | 35 | 54 | 85 | 0 |
| 19 | 2,5,2',5' | 90 | 95 | >99 | >95 |
| 20 | 2,4,2',5' | 65 | 80 | >99 | >95 |
| 21 | 2,4,2',4' | 0 | 0 | >98 | >70 |
| 22 | 2,4,5,2' | >99 | >99 | 80 | 90 |
| 23 | 2,3,2',5' | 80 | >99 | >99 | >98 |
| 24 | 3,4,4'/2,3,2',4' | 30 | 50 | 85 | >98 |
| 25 | 2,3,4,2'/2,3,6,4'/2,6,3',4' | 20 | 25 | 65 | 45 |
| 26 | 2,3,2',3' | 95 | >99 | 95 | 95 |
| 27 | 2,4,5,4' | 0 | 0 | 25 | 0 |
| 28 | 2,5,3',4' | 65 | 65 | >99 | >97 |
| 29 | 2,4,3',4'/2,3,6,2',5' | 20 | 15 | 50 | 15 |
| 30 | 2,3,6,2',4' | 25 | 20 | 50 | 20 |
| 31 | 2,3,3',4'/2,3,4,4' | 0 | 0 | 45 | 0 |
| 32 | 2,3,6,2'3'/2,3,5,2',5' | 25 | 25 | 90 | >98 |
| 33 | 2,3,5,2',4'/2,4,5,2',5' | 35 | 25 | 95 | >97 |
| 34 | 2,4,5,2',4' | 0 | 0 | 50 | 30 |
| 35 | 2,4,5,2',3'/2,3,5,6,2',6' | 0 | 0 | 55 | 0 |
| 36 | 2,3,4,2',5' | 25 | 0 | 80 | 60 |
| 37 | 2,3,4,2',4' | 25 | 0 | 40 | 0 |
| 38 | 2,3,6,3',4'/3,4,3',4' | 0 | 0 | 45 | 0 |
| 39 | 2,3,4,2',3' | 0 | 0 | 55 | 25 |
| 40 | 2,3,6,2',4'5'/2,4,5,3',4' | 0 | 0 | 35 | 0 |
| 41 | 2,3,4,3',4'/2,3,4,2',3',6 | 0 | 0 | 0 | 0 |
| Total | Degradation | 60% | 65% | 77% | 34% |

[a]resting cell assays- % degradation of individual congeners by live bacteria compared to killed bacteria after 2 day incubation with 10 ppm Aroclor 1242.
[b]Growing cell assays- % degradation by B30P4::TnPCB and 1PL.5::TnPCB in minimal salts media with 2000 ppm surfactant and 25 ppm Aroclor 1242 after a 20 day incubation.
[c]Surfactant/PCB Washate- PCBs were washed from a contaminated soil with the surfactant. The surfactant was diluted 1:5 to give an initial concentration of 2000 ppm surfactant, and 10 ppm PCB. Nutrients and B30P4::TnPCB and 1PL5::TnPCB were added. % Degradation was determined after a 20 day incubation.
*—These congeners were not present in the PCB contaminated soil or washate.

Desolubilization of PCBs via Surfactant Degradation.

The surfactant derived from the soil washing experiment was subsequently used for desolubilization experiments. The soil wash solution was adjusted to pH 7 and amended with nutrients and diatomaceous earth as discussed above. Triplicate tubes were immediately centrifuged and the supernatant analyzed for soluble PCB and surfactant by the previously described method (time 0, FIG. 5). Triplicate tubes were also inoculated with *Pseudomonas putida* IPL5::TnPCB and *Alcaligenes eutrophus* B30P4::TnPCB (E, FIG. 5). After incubation, the experimental tubes were centrifuged, and surfactant and PCBs in the supernatant were analyzed as described above.

Figure 5:
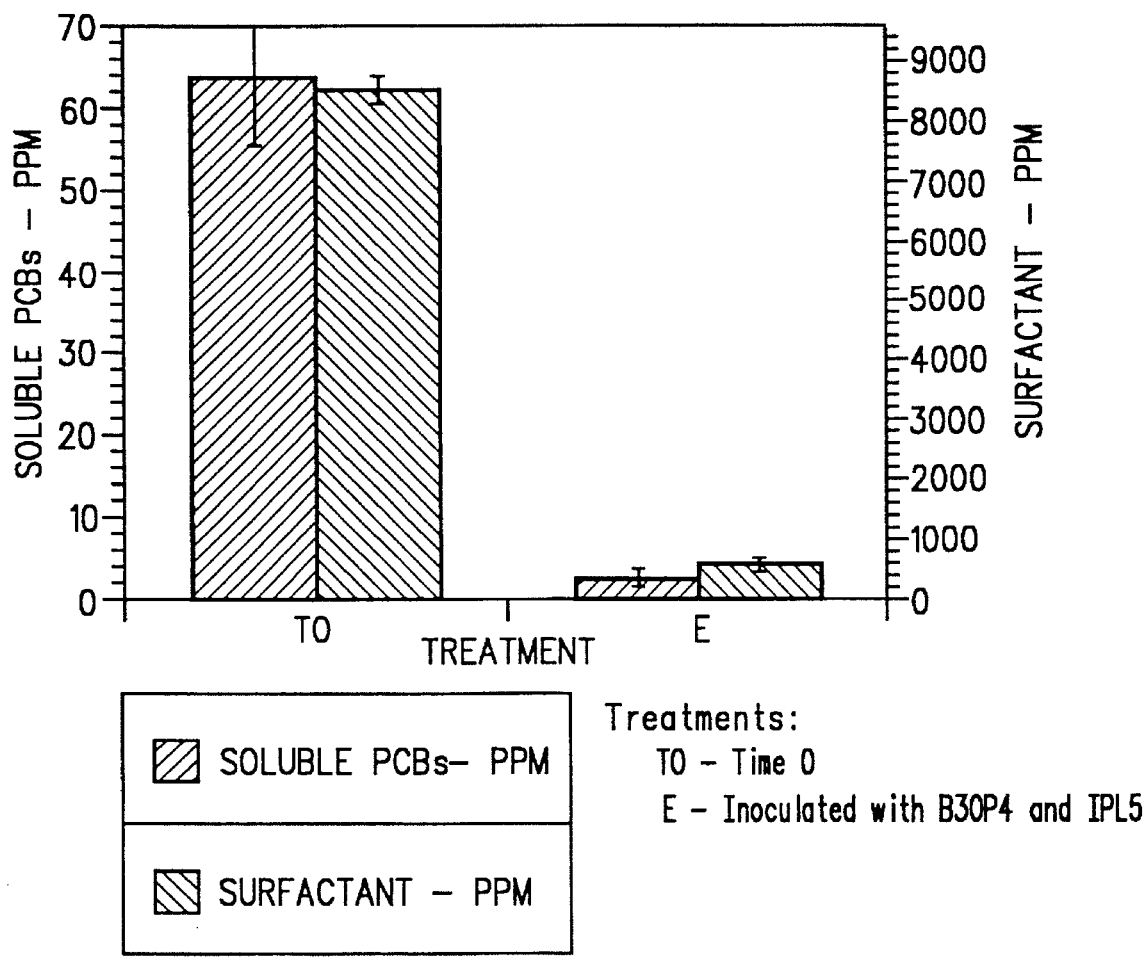
FIG. 5 is a graph showing PCB desolubilization via surfactant degradation.

At time 0 the PCB and surfactant concentrations in the supernatant were 63.6 ppm (SD 6.8) and 8433 ppm (SD 170), respectively. After incubation the PCB and surfactant concentrations in the supernatant were 2.7 ppm (SD 0.6) and 564 ppm (SD 44), respectively. The data is shown in FIG. 5. These results indicate that surfactant degradation resulted in desolubilization of the majority of PCB previously removed from the soil by surfactant washing, and the PCB were thereby concentrated on a much smaller volume of diatomaceous earth and spent cells.

The subject invention provides a biologically based means of PCB destruction to clean contaminated soils. The integrated approach of the subject application provides an economical and environmentally desirable means of PCB bioremediation.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for bioremediation of soil contaminated with PCBs, the method comprising:

washing said soil with a biodegradable surfactant whereby said PCBs are solubilized;

removing effluent comprising said surfactant and said solubilized PCBs to a bioreactor comprising an inert substrate, wherein said effluent enters the bioreactor at a rate such that surfactant concentration in the reactor is maintained at about the critical micellar concentration;

inoculating said bioreactor with a microbial strain capable of utilizing surfactant as an energy source and biodegrading said surfactant, and capable of biodegrading PCBs to their corresponding chlorobenzoic acids;

growing said microbial strain for a period of time sufficient to biodegrade said surfactant, and to produce chlorobenzoic acid degradation products from said PCBs; wherein residual undegraded PCBs are deposited on an inert substrate; and removing said inert substrate and residual undegraded PCBs.

2. A method according to claim 1, further comprising the steps of:

chlorobenzoic acid degradation by naturally occurring or added microbial strains.

3. A method according to claim 1, further comprising the steps of:

removing said inert substrate and residual undegraded PCBs to a second bioreactor comprising microbes capable of biphenyl co-metabolism of PCBs; and biodegrading said PCBs to their corresponding chlorobenzoic acids.

4. A method according to claim 1, further comprising the steps of:

removing said inert substrate and residual undegraded PCBs to a second bioreactor comprising microbes capable of anaerobic dehalogenation of PCBs; and reducing the chlorine content of said residual undegraded PCBs.

5. A method for bioremediation of soil contaminated with PCBs, the method comprising:

washing said soil with a biodegradable surfactant whereby said PCBs are solubilized;

removing effluent comprising said surfactant and said solubilized PCBs to a bioreactor comprising an inert substrate, wherein said effluent enters the bioreactor at a rate such that surfactant concentration in the reactor is maintained at or below the critical micellar concentration;

inoculating said bioreactor with a microbial strain capable of biodegrading said surfactant, and capable of biodegrading PCBs to their corresponding chlorobenzoic acids, wherein said microbial strain comprises an exogenous DNA vector having bacterial bphABCD genes under the regulatory control of a constitutive promoter;

growing said microbial strain for a period of time sufficient to biodegrade said surfactant, and to produce chlorobenzoic acid degradation products from said PCBs; wherein residual undegraded PCBs are deposited on an inert substrate; and removing said inert substrate and residual undegraded PCBs.

6. A method according to claim 5, wherein said microbial strain is capable of degrading both hydrophilic and hydrophobic moieties of alkylethoxylate surfactants.

7. A method according to claim 5, where said microbial strain is *Alcaligenes eutrophus* B30P4.

8. A method according to claim 5, wherein said microbial strain is *Pseudomonas putida* IPL5.

* * * * *